United States Patent [19]

Remy

[11] 4,022,902

[45] May 10, 1977

[54] 10,11-DIHYDRO-3-CARBOXYCYPROHEP-TADIEN-N-OXIDE

[75] Inventor: David C. Remy, North Wales, Pa.

[73] Assignee: Merck & Co., Inc., Rahway, N.J.

[22] Filed: Aug. 29, 1975

[21] Appl. No.: 608,944

[52] U.S. Cl. .............................. 424/267; 260/293.62
[51] Int. Cl.$^2$ ........................................ C07D 211/94
[58] Field of Search ............... 260/293.62; 424/267

[56] References Cited

UNITED STATES PATENTS 3,014,911  12/1961  Engelhardt .................... 260/293

3,981,877  9/1976  Plugh ............................ 260/293.62

*Primary Examiner*—G. Thomas Todd
*Attorney, Agent, or Firm*—William H. Nicholson; Harry E. Westlake, Jr.; James A. Arno

[57] ABSTRACT

The N-oxide of 10,11-dihydro-3-carboxycyproheptadine is disclosed to have pharmaceutical utility as an appetite stimulant and as an antihistaminic agent. Also disclosed are processes for the preparation of such compound; pharmaceutical compositions comprising such compound; and methods of treatment comprising administering such compound and compositions.

3 Claims, No Drawings

10,11-DIHYDRO-3-CARBOXYCYPROHEPTADIEN-N-OXIDE

BACKGROUND OF THE INVENTION

This invention relates to 10,11-dihydro-3-carboxycyproheptadine-N-oxide (1-methyl-1-oxo-4-(3-carboxy-10,11-dihydro-5H-dibenzo[a,d]cyclohepten-5-ylidene) piperdine) as an appetite stimulant and as an antihistaminic agent; also contemplated within the scope of the present invention are the pharmaceutically acceptable salt, ester and amide derivatives of such compound. Further, this invention relates to processes for the preparation of such compounds; to pharmaceutical compositions comprising such compounds; and to methods of treatment comprising administering such compounds and compositions when an appetite stimulant and/or antihistamine effect is indicated. The free acid form of the 10,11-dihydro-3-carboxycyproheptadine-N-oxide of the present invention has the following structural formula (I):

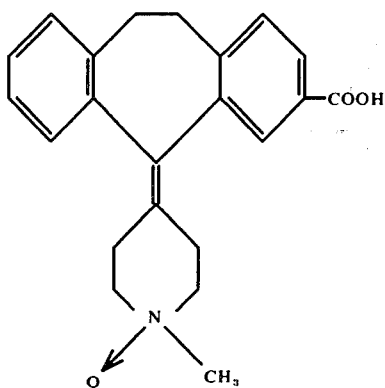

Unexpectedly, it has been discovered that the 10,11-dihydro-3-carboxycyproheptadine-N-oxides of the present invention are appetite stimulants and antihistaminics substantially devoid of other pharmacological effects such as anticholinergic activity, which latter activity is so characteristic of compound structurally related to cyproheptadine, including dihydro derivatives thereof. Accordingly, it is an object of the present invention to provide 10,11-dihydro-3-carboxycyproheptadine-N-oxide and its pharmaceutically acceptable salt, ester and amide derivatives as appetite stimulants and antihistaminic agents. It is a further object of this invention to provide processes for the preparation of such compounds; pharmaceutical compositions comprising such compounds; and methods of treatment comprising administering such compounds and compositions when an appetite stimulant and/or antihistaminic effect is indicated.

DETAILED DESCRIPTION OF THE INVENTION

The 10,11-dihydro-3-carboxycyproheptadine-N-oxides of the present invention may conveniently be prepared from 3-bromo-10,11-dihydro-5H-dibenzo[a,d]cyclohepten-5-one [see, for example, U.S. Pat. Nos. 3,306,934 and 3,014,911 and co-pending, commonly assigned U.S. patent application of David C. Remy, Ser. No. 563,285 (filed Mar. 28, 1975) which is a continuation-in-part of now abandoned Ser. No. 522,676 filed Nov. 11, 1974, which patents and applications are incorporated herein by reference] by reaction with 1-methyl-4-piperidylmagnesium halide in a suitable solvent such as tetrahydrofuran and the like to provide 1-methyl-4-(3-bromo-10,11-dihydro-5-hydroxy-5H-dibenzo-[a,d]cyclohepten-5-yl)piperidine, which is dehydrated on treatment with a suitable dehydrating agent such as a mineral acid and the like to provide 1-methyl-4-(3-bromo-10,11-dihydro-5H-dibenzo[a,d]cyclophepten-5-ylidene)piperidine, which on conversion to the 3-cyano species by treatment with cuprous cyanide followed by hydrolysis yields the desired intermediate 1-methyl-4-(3-carboxy-10,11-dihydro-5H-dibenzo[a,d]cyclohepten-5-ylidene)-piperidine(10,11-dihydro-3-carboxycyproheptadine). Alternatively, the Grignard reactions may follow the reaction with cuprous cyanide on the ketone; thus the next following treatment with mineral acid not only dehydrates but also converts the 3-cyano substituent into the desired 3-carboxyl function. The resulting 10,11-dihydro-3-carboxycyproheptadine is then oxidized to the desired N-oxide of the present invention. Preferably, however, the oxidation is conducted upon a suitable lower alkyl ester of the intermediate free acid which is prepared by conventional techniques. For example, the ethyl ester may be conveniently be prepared by reacting the free acid in ethanol in the presence of $BF_3(CH_3CH_2)_2O$. Hydrogen peroxide is a suitable oxidizing agent, and the reaction may be conducted in any suitably inert protic solvent such as aqueous methanol, aqueous ethanol or the like at a temperature of from 0° to reflux for from 1 to 72 hours. The following diagrams illustrates these processes.

SCHEME I

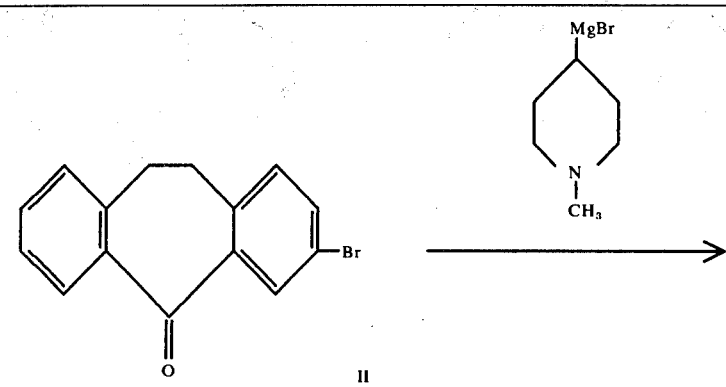

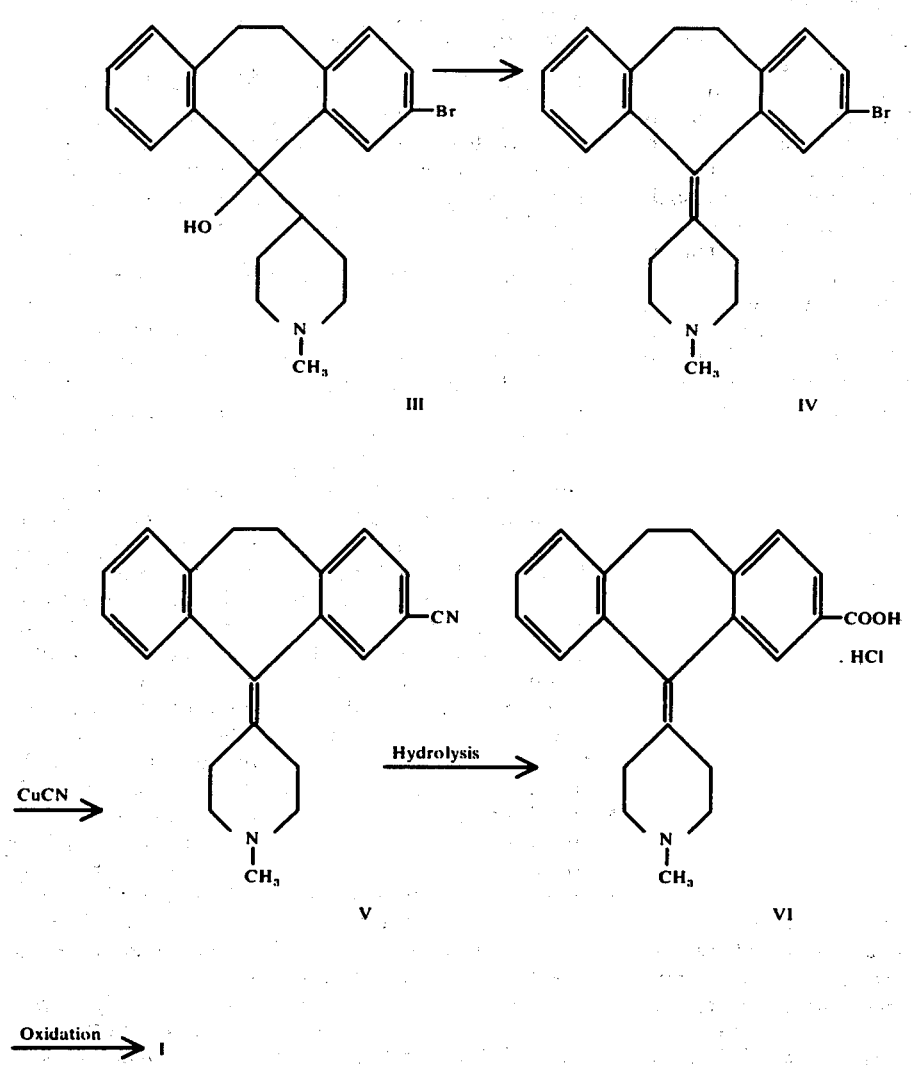
SCHEME II
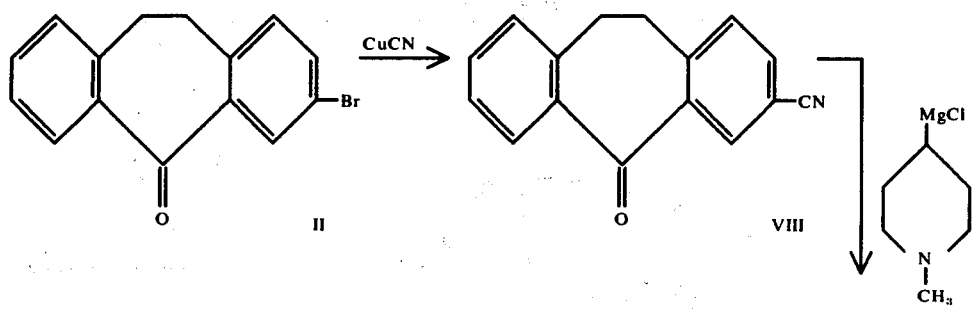

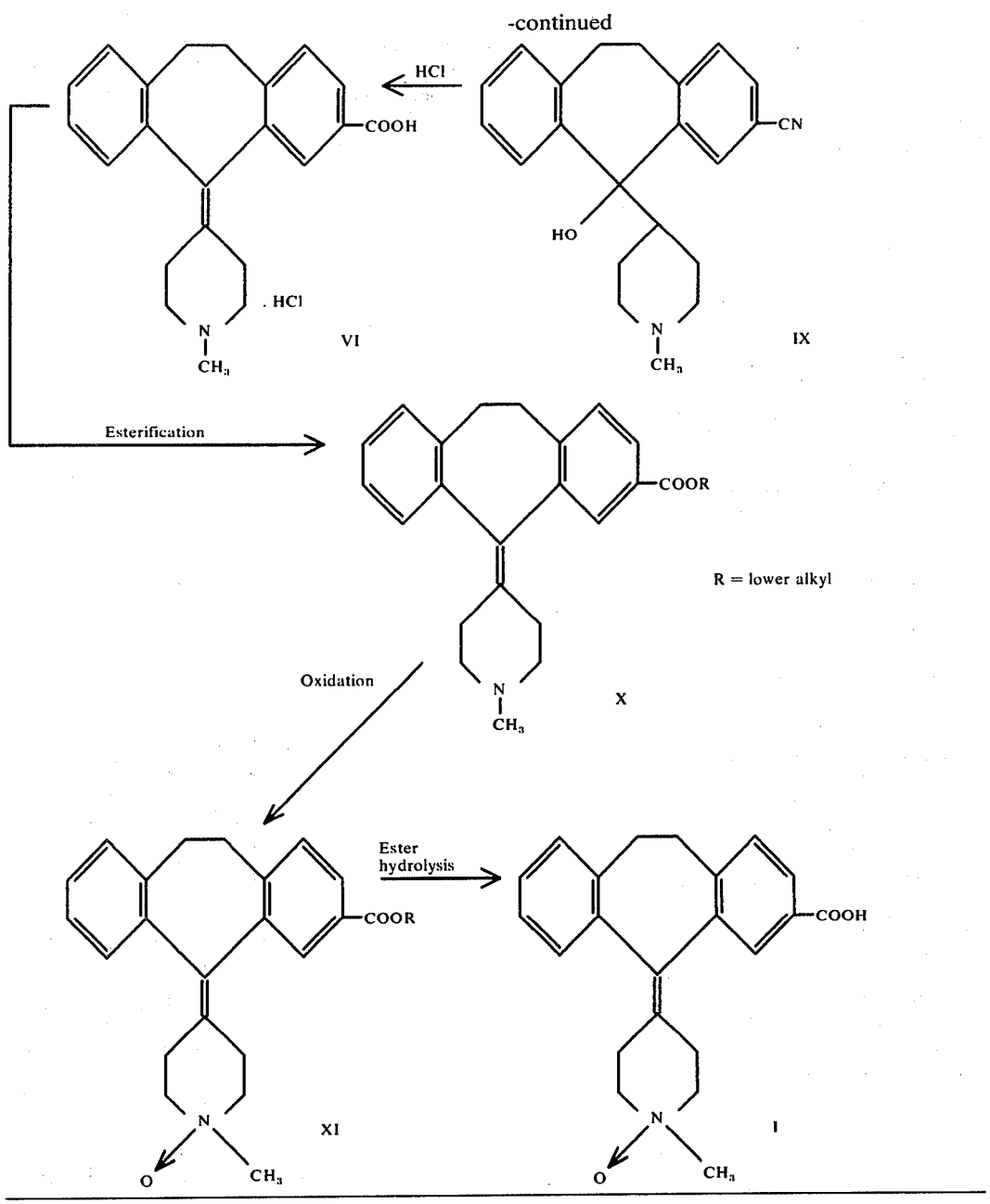

Suitable pharmaceutical salt, ester and amide forms of 10,11-dihydro-3-carboxycyproheptadine-N-oxide of the present invention may be prepared by conventional means. Salt forms are the most preferred and include (relative to the nitrogen atom of the piperidyl moiety): the hydrochloride, sulfate, phosphate, citrate, tartrate, succinate and the like; with respect to salts based upon the carboxy function, salts derived from the alkali and alkaline earth metals such as sodium and potassium are preferred. These salts are generally equivalent in potency to the free acid form taking into consideration the stoichiometric quantities employed.

In the method of treatment and pharmaceutical composition aspects of the present invention it is noted that the precise unit dosage form and dosage level depend upon the case history of the individual being treated and consequently are left to the discretion of the therapist. In general, however, the compounds of the present invention produce the desired effect of appetite stimulation when given at from about 0.01 to about 10.0 mg. per kg. body weight per day. The preferred form of delivery of the instant compounds for appetite stimulation of domestic animals is by solution in drinking water or preformulated feedstuffs. For human and animal administration, any of the usual pharmaceutical oral forms may be employed such as tablets, elixirs and aqueous suspension comprising from about 0.01 to about 10.0 mg. of the compounds of this invention per kg. body weight given daily. Thus, for example, tablets given 2–4 times per day comprising from about 0.5 to about 50 mg. of the compounds of this invention are suitable for human treatment. Sterile solutions (representatively given for human treatment) for injection comprising from about 0.1 to about 10.0 mg. of the compounds of this invention given two to four times daily are also suitable means of delivery. When an antihistaminic effect is indicated, the above recited dosage forms and levels are also appropriate.

The following examples representatively illustrate but do not limit the product, compositional or method of treatment aspect of the present invention.

EXAMPLE I

Preparation of
1-methyl-1-oxo-4-(3-carboxy-10,11-dihydro-5H-dibenzo[a,d]cyclohepten-5-ylidene)piperidine

Step A

1-Methyl-4-(3-bromo-10,11-dihydro-5H-dibenzo[a,d-]cyclohepten-5-ylidene)piperidine To an ice-cooled solution of 15.0 gm. (0.0523 mole) of 3-bromo-10,11-dihydro-5H-dibenzo[a,d]cyclohepten-5-one in 150 ml. of dry tetrahydrofuran is added dropwise over 0.5 hr., 100 ml. of 0.53M 1-methyl-4-piperidylmagnesium chloride in tetrahydrofuran. The solution is stirred for one hour, and then the tetrahydrofuran is removed on a rotary evaporator. The red-oily residue that remains is dissolved in benzene and water is added dropwise until a clear benzene supernatant and a gelatinous aqueous phase is obtained. The benzene is decanted and the gelatinous aqueous phase is extracted with two 100 ml. portions of hot benzene. The combined benzene phases are washed with six 200 ml. portions of water and then the benzene phase is evaporated on a rotary evaporator. The residue that remains is triturated with acetonitrile. The crystalline product is removed by filtration, washed with additional acetonitrile, collected and dried at 60° C. The product 1-methyl-4-(3-bromo-10,11-dihydro-5-hydroxy-5H-dibenzo[a,d]cyclohepten-5-yl)piperidine, 9.66 gm. (65%) melts at 203°–207° C.

A mixture of 9.66 gm. of 1-methyl-4-(3-bromo-10,11-dihydro-5-hydroxy-5H-dibenzo[a,d]cyclohepten-5-yl)piperidine and 130 ml. of 6N hydrochloric acid is stirred and refluxed for 0.5 hr. The bulk of the hydrochloric acid is removed on a rotary evaporator and the residue is partitioned between 5% aqueous sodium hydroxide and ether. The ether phase is removed, washed with water, dried over magnesium sulfate, filtered, and the ether removed to give 9.17 gm. of 1-methyl-4-(3-bromo-10,11-dihydro-5H-dibenzo[a,d]cyclohepten-5-ylidene)piperidine.

Step B

1-Methyl-4-(3-cyano-10,11-dihydro-5H-dibenzo[a,d-]cyclohepten-5-ylidene)piperidine A mixture of 9.17 gm. (0.0249 mol) of 1-methyl-4-(3-bromo-10,11-dihydro-5H-dibenzo[a,d]cyclohepten-5-ylidene)piperidine, 4.58 gm. (0.0498 mol) of cuprous cyanide, and 30 ml. of dry dimethylformamide is stirred and heated under reflux for 6.5 hr. To the cooled solution (25° C) is added 54 ml. of water, 27 ml. of a saturated aqueous solution of sodium cyanide, and 75 ml. of benzene. The mixture is stirred until a two phase system is obtained. The benzene phase is removed and the aqueous phase is extracted with two 75 ml. portions of benzene. The combined benzene phases are washed with 100 ml. of aqueous 0.1M sodium cyanide, three 100 ml. portions of water, and dried over magnesium sulfate. After filtering, evaporation of the benzene gives 7.40 gm. of a crystalline residue. This material is dissolved in the minimum volume of chloroform and passed over an alumina column (15 inches × 1 inch) packed in chloroform. The column is eluted with chloroform. Evaporation of the chloroform gives a crystalline product that is recrystallized from isopropyl alcohol to give pure 1-methyl-4-(3-cyano-10,11-dihydro-5H-dibenzo[a,d]cyclohepten-5-ylidene)piperidine, m.p. 152°–154° C.

Analysis Calc. for: $C_{22}H_{22}N_2$: Calc.: C, 84.04; H, 7.05; N, 8.91. Found: C, 83.87; H, 7.41; N, 8.73.

Step C

1-Methyl-4-(3-carboxy-10,11-dihydro-5H-dibenzo[a,d]cycohepten-5-ylidene)piperidine hydrochloride A mixture of 1.0 gm. (0.00318 mol) of 1-methyl-4-(3-cyano-10,11-dihydro-5H-dibenzo[a,d]cyclohepten-5-ylidene)piperidine and 20 ml. of 6N hydrochloric acid is stirred and refluxed for 18 hours. After cooling, the mixture is filtered, and the collected solid is washed with 6N hydrochloric acid and then with ethanol. The dried material weighs 1.03 gm (87%). Recrystallization from absolute ethanol gives pure 1-methyl-4-(3-carboxy-10,11-dihydro-5H-dibenzo[a,d]cyclohepten-5-ylidene)piperidine hydrochloride, m.p. 304°–307° C.

Analysis Calc. for: $C_{22}H_{23}NO_2.HCl$: Calc.: C, 71.43; H, 6.54; N, 3.79; Cl, 9.59. Found: C, 71.01; H, 6.87; N, 3.73; Cl, 9.44.

Step D:

1-Methyl-1-oxo-4-(3-carboxy-10,11-dihydro-5H-dibenzo[a,d]cyclohepten-5-ylidene)piperidine Following the esterification and oxidation procedures of Example 2 (infra) the product of Example 1, Step C is converted to the corresponding N-oxide, 1-methyl-1-oxo-4-(3-carboxy-10,11-dihydro-5H-dibenzo[a,d]cyclohepten 5-ylidene)piperidine.

EXAMPLE 2

Preparation of
1-Methyl-1-oxo-4-(3-carboxy-10,11-dihydro-5H-dibenzo[a,d]cyclohepten-5-ylidene)piperidine A solution of 4.13 gm. (0.0177 mol) of 3-cyano-10,11-dihydro-5H-dibenzo[a,d]cyclohepten-5-one (prepared from the 3-bromo ketone by reaction with CuCN according to the procedure of Example 1, Step B, when the appropriate substitution of reactants is made) in 40 ml. of tetrahydrofuran is treated with 42 ml. of 0.43M 1-methyl-4-piperidylmagnesium chloride. The solution is stirred for one hour, and then the tetrahydrofuran is removed on a rotary evaporator. The red-oily residue that remains is dissolved in benzene and water is added dropwise until a clear benzene supernatant and a gelatinous aqueous phase is obtained. The benzene is decanted and the gelatinous aqueous phase is extracted with two 100 ml. portions of hot benzene. The combined benzene phases are washed with six 200 ml. portions of water and then the benzene phase is evaporated on a rotary evaporator. The residue that remains is triturated with acetonitrile. The crystalline product is removed by filtration, washed with additional acetonitrile collected and dried at 60° C. to give 2.88 g. (49%) of crystalline IX (Scheme II, chart supra) which is mixed with 60 ml. of 6N hydrochloric acid and refluxed 24 hours to give 2.80 gm. of VI (Scheme II, supra). A mixture of 2.80 gm. of VI and 2 ml. of boron trifluoride-etherate in 200 ml. of absolute ethanol is refluxed for 8 hours. The solution is evaporated to dryness and the residue is partitioned between ether and aqueous sodium carbonate solution.

The ether phase is removed, dried over magnesium sulfate, filtered and the ether is removed by evaporation. There is obtained 2.7 gm. of the ethyl ester X (Scheme II, supra) that is dissolved in 100 ml. of methanol, 10 ml. of water and 10 ml. of 30% hydrogen peroxide. After stirring for 48 hours at room temperature, a small scoop of 5% Pt/C is added and the mixture is stirred an additional 2 hours to decompose the excess hydrogen peroxide. The mixture is filtered and the solvent is evaporated to give chromatographically pure ethyl ester -N-oxide XI (Scheme II, supra). One gram of ethyl ester -N-oxide XI is dissolved in 10 ml. of methanol containing 2 ml. of 2N potassium hydroxide. The solution is heated on the steam bath for 2 hours. The methanol is removed, 10 ml. of water is added to the residue, and, while stirring, glacial acetic acid is added dropwise until no further precipitate forms. The white solid that forms is removed by filtration and is washed thoroughly with water. The product is collected and dried to give I sesquihydrate; m.p. 208–209° )dec., foams); tlc homogenous.

Analysis calcd. for $C_{22}H_{23}NO.1\ 1/2\ H_2O$: Calc.: C, 70.19; H, 6.96; N, 3.72. Found: C, 70.30; H, 6.77; N, 3.51.

EXAMPLE 3

Pharmaceutical compositions

A typical tablet containing 1 mg. 10,11-dihydro-3-carboxycyproheptadine-N-oxide per tablet is prepared by mixing together with the active ingredient calcium phosphate, lactose and starch in the amounts shown in the tablets below. After these ingredients are thoroughly mixed, the appropriate amount of magnesium stearate is added and the dry mixture blended for an additional three minutes. This mixture is then compressed into tablets weighing approximately 124 mg. each. Similarly prepared are tablets containing 10,11-dihydro-3-carboxycyproheptadine -N-oxide hydrochloride.

| TABLET FORMULA | |
|---|---|
| INGREDIENT | MG. PER TABLET |
| 10,11-dihydro-3-carboxycyproheptadine-N-oxide | 1 mg. |
| Calcium phosphate | 52 mg. |
| Lactose | 60 mg. |
| Starch | 10 mg. |
| Magnesium stearate | 1 mg. |
| 10,11-dihydro-3-carboxycyproheptadine-N-oxide hydrochloride | 1 mg. |
| Calcium phosphate | 52 mg. |
| Lactose | 60 mg. |
| Starch | 10 mg. |
| Magnesium stearate | 1 mg. |

What is claimed is:

1. A method of producing an appetite stimulant and/or antihistaminic effect comprising administering in unitary dosage form a therapeutically effective amount of 10,11-dihydro-3-carboxycyproheptadine-N-oxide or a nontoxic pharmaceutically acceptable salt thereof.

2. A pharmaceutical composition comprising a therapeutically effective amount in unitary dosage form of 10,11-dihydro-3-carboxycyproheptadine-N-oxide or a nontoxic pharmaceutically acceptable salt thereof and a pharmaceutical carrier therefor.

3. 10,11-Dihydro-3-carboxycyproheptadine-N-oxide or a nontoxic pharmaceutically acceptable salt thereof.

* * * * *